Figure 1:
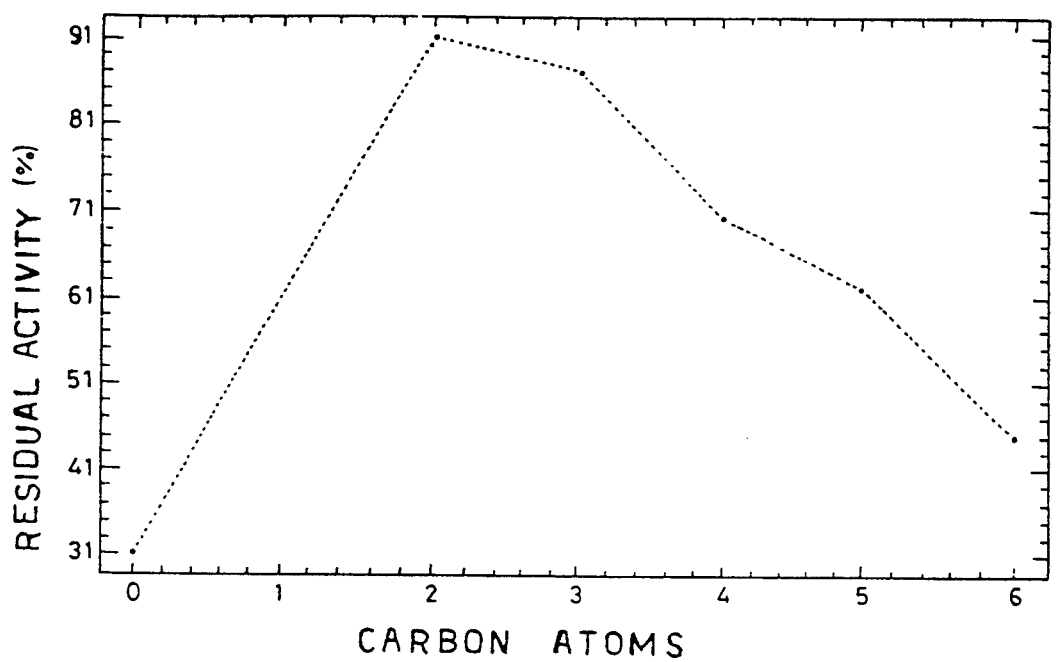

United States Patent [19]

D'Alterio et al.

[11] Patent Number: 5,266,472
[45] Date of Patent: Nov. 30, 1993

[54] STABILIZATION OF THE ENZYME URATE OXIDASE IN LIQUID FORM

[75] Inventors: Maurizio D'Alterio, Brugherio; Dario Frontini, Milan; Mauro Papagni, Busto Arsizio, all of Italy

[73] Assignee: Instrumentation Laboratory S.R.L., Milan, Italy

[21] Appl. No.: 880,057

[22] Filed: May 7, 1992

[30] Foreign Application Priority Data

May 17, 1991 [IT] Italy .................. MI 91 A 001366

[51] Int. Cl.[5] .................. C12Q 1/62; C12N 9/96; C12N 9/02; C12N 9/06
[52] U.S. Cl. .................. 435/188; 435/10; 435/189; 435/191
[58] Field of Search .................. 435/10, 188, 189, 191

[56] References Cited

U.S. PATENT DOCUMENTS

| | | | |
|---|---|---|---|
| 3,862,885 | 1/1975 | Kano et al. | 435/10 |
| 4,094,744 | 6/1978 | Hartdegen et al. | 435/182 |
| 4,247,630 | 1/1981 | Ziegenhorn et al. | 435/10 |
| 4,378,435 | 3/1983 | Takagi et al. | 435/180 |
| 4,766,106 | 8/1988 | Katre et al. | 514/12 |
| 4,781,890 | 11/1988 | Arai et al. | 422/56 |
| 4,917,880 | 4/1990 | Wretlind et al. | 424/5 |
| 5,053,225 | 10/1991 | Miyasaka et al. | 424/85.8 |
| 5,116,729 | 5/1992 | Ismail et al. | 435/14 |

FOREIGN PATENT DOCUMENTS 0080304 6/1983 European Pat. Off. .

OTHER PUBLICATIONS

Wang et al. (1988) *J. Parenteral Sci. Tech.* (Supp.), 42, S1-S26.

*Primary Examiner*—Douglas W. Robinson
*Assistant Examiner*—Jon P. Weber
*Attorney, Agent, or Firm*—Testa, Hurwitz & Thibeault

[57] ABSTRACT

This invention relates to a process for stabilizing the enzyme urate oxidase (commonly known as uricase) in liquid form, and to the relative compositions which can then be obtained, with particular reference to compositions containing a Trinder reagent. According to the process of the invention, uricase can be stabilized in liquid form by adding to the composition containing the enzyme a substituted or unsubstituted dicarboxylic acid containing from 2 to 5 carbon atoms, and preferably 4 or 5. Aspartic acid has shown to be particularly effective in providing said stabilizing activity in liquid uricase compositions containing a Trinder reagent.

20 Claims, 1 Drawing Sheet

STABILIZATION OF THE ENZYME URATE OXIDASE IN LIQUID FORM

Urate oxidase, commonly known as uricase and so called hereinafter, is an enzyme present in the liver, spleen and kidney of most mammals with the exception of man, and in the presence of oxygen converts uric acid to allantoin with the development of hydrogen peroxide, in accordance with the following reaction:

$$\text{Uric acid} + 2H_2O + O_2 \xrightarrow{\text{uricase}} \text{Allantoin} + H_2O_2 + CO_2$$

Uricase of mainly microbic origin is commonly used in clinical analysis laboratories for determining uric acid in biological liquids.

Uric acid is the final product of purine catabolism and is found in the blood and urine, as man is unable to further catabolize it. Methods for determining uric acid in biological fluids assume particular clinical importance in relation to situations of excessive production or reduced secretion, which cause it to accumulate in the blood (so-called hyperuricemia). A classic example of this pathological situation is represented by gout in which, following increase in uric acid concentration, sodium urate crystals precipitate in the cartilage.

One method commonly used for clinically determining uric acid in the serum uses the above reaction in combination with a second reaction (such as a so-called Trinder reaction) leading to the formation of a photometrically measurable coloured compound. As in the case of all enzymes, uricase is of poor stability and is therefore normally marketed in solid form as a lyophilized powder. Although having lower enzyme stability than the solid form, liquid formulations are easier to produce, offer less risk to the personnel involved because of the limited contact with sensitizing and toxic powders, and are more comfortable to use.

The importance of achieving a liquid formulation of the enzyme uricase which does not involve costly production methods, avoids risks to persons producing or using the enzyme, and simplifies its use (for example by reducing the time required for preparing the reagent), is therefore apparent.

Known uricase solutions are described for example in H. U. Bergmeyer (ed), Methods and Enzymatic Analysis, Vol. VII, 3rd edit., VCH Verlagsgesellschaft, Weiheim 1985, p. 323, where it describes a 50% aqueous glycerin solution containing 50 mM of glycine and 130 mM of sodium carbonate at pH 10.2, stated to be stable for some months at 4° C.

The company Enzymatic Ltd. of Cambridge (U.K.) produces a uricase composition in 50 mM phosphate buffer at pH 7.5, states to be stable for some months both at 4° C. and at ambient temperature. The enzyme is however less stable at higher temperatures, so exposing the clinical operator to the risk of reduced or even no activity following changes in the enzyme storage temperature which can occur during transport by common non-refrigerated means of transport or during the storage of the enzyme before use. Experiments have also been conducted on the stabilizing effects of various substances. For example, a large family of compounds including carboxylic acids are mentioned in the article Wiseman, A Proc. Biochem. August 1973, page 14 as able to provide stabilizing effects in specific cases. No correlation has however been found between the stabilizing activity of these agents and specific enzymes, and in fact it is explicitly recognized that the effect of carboxylic acids and other agents on enzymes (cross-linking) in many cases leads not to stabilization but on the contrary to enzyme inactivation.

An object of the present invention is therefore to provide a method for stabilizing a preparation of the enzyme uricase in liquid form, such that the preparation has greater stability over time, economy of production and ease of use than previously proposed products.

A further and more detailed object of the present invention is to provide a method for stabilizing uricase in ready-to-use single-reagent solutions containing the reactants necessary for using the hydrogen peroxide evolved during the reaction catalyzed by the enzyme, for the analytical determination of the initial uric acid. Specifically, it has been sought to provide a method for stabilizing the enzyme uricase which can reduce interference with the enzyme peroxidase to a minimum so as to enable uricase to be used in reagents for determining uric acid by the so-called Trinder method (in which the use of the enzyme peroxidase is essential).

In this respect, the present invention relates to the preparation of a liquid composition of the enzyme uricase from which a time-stable preparation ready for immediate use can be obtained. According to the invention, the method for obtaining a stabilized liquid preparation of the enzyme uricase is characterised by introducing into the preparation an unsubstituted or substituted dicarboxylic acid containing from 2 to 5 carbon atoms, and preferably 4 or 5.

The ready-to-use stabilized liquid preparation of the enzyme uricase according to the invention is characterised by comprising a substituted or unsubstituted dicarboxylic acid containing from 2

In this respect, it has been surprisingly found that the addition of a $C_2$–$C_5$ dicarboxylic acid, which may be substituted, in a concentration exceeding 500 mM to a solution in which the enzyme uricase is dissolved has the unexpected effect of stabilizing the enzyme in liquid preparations.

By way of example, some examples are given hereinafter of preparations according to the invention, on which tests have been carried out allowing those properties related to the objects of the invention to be identified.

Figure 2:
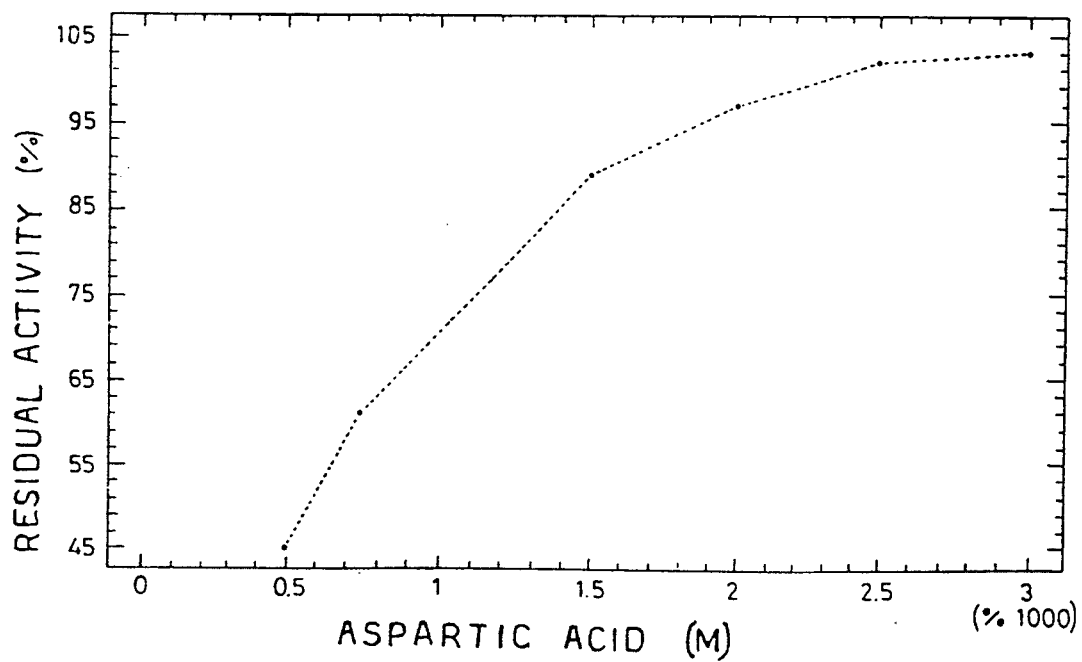

The experimental results are illustrated with reference to tables and the accompanying figures, in which:

FIG. 1 is a graph showing uricase stability as a function of the number of carbon atoms in the dicarboxylic acids added to the solution, and FIG. 2 is a graph showing the stability of a uricase solution as a function of aspartic acid concentration.

EXAMPLE 1

The uricase activity was determined by adding 0.05 ml of a solution containing the enzyme, possibly diluted with borate buffer to 0.2–0.5 U/ml, to 3 ml of a 0.13 mM uric acid solution in 0.02 M borate buffer at pH 9.0, at a temperature of 37° C.

The conversion of the uric acid to allantoin in accordance with the aforesaid reaction was followed at 292 nm for 3 minutes. In the graph of FIG. 1, unsubstituted dicarboxylic acid was added to a final concentration of 750 mM and pH 8 in all cases and the residual activity was measured by an accelerated stability test after the solution had remained at 60° C. for 40 minutes. The horizontal axis represents the number of acid carbon atoms, from 2 to 5, with 0 conventionally indicating the absence of added carboxylic acid, whereas the vertical axis represents the residual activity expressed as a percentage of the initial activity.

The following carboxylic acids, containing from 2 to 5 carbon atoms respectively, were added: oxalic acid, malonic acid, succinic acid, glutaric acid and adipic acid.

From said graph it can be seen that the enzyme activity recovery peak corresponds to oxalic acid.

Within the pH range of 6.5–10, pH 8 was identified as the value about which the enzyme stabilization activity is optimized. The experiments also showed that the ratio of millimoles/liter of stabilizer to units/liter of enzyme can vary from 1:3 to 1:0.2 without any appreciable change in enzyme stability being noted. For solutions with enzyme concentrations of practical use, i.e., between 100 U/l and 1000 U/l, a dicarboxylic acid concentration of 500 mM was identified as the value about which the stabilizing activity of the dicarboxylic acid on the enzyme begins substantially to appear.

Again, a dicarboxylic acid concentration of 750 mM was identified as the value about which the stabilizing activity of the dicarboxylic acid on the enzyme is satisfactory for practical purposes.

EXAMPLE 2

In addition to the unsubstituted dicarboxylic acid molecules mentioned in Example 1, substituted dicarboxylic acid molecules such as tartaric acid and aspartic acid were also tested.

FIG. 2 shows the graph of uricase accelerated activity as a function of aspartic acid concentration. This graph was obtained by measuring the uricase activity after incubating two uricase solutions with different concentrations of aspartic acid, a $C_4$ dicarboxylic acid substituted in position 2 with an amino group, for 40 minutes at 60° C.

The uricase activity was determined as in Example 1.

From said graph it can be seen that stabilizing activity on the activity of the uricase in solution begins at an aspartic acid concentration of about 500 mM.

EXAMPLE 3

The stabilizing effect of aspartic acid can be clearly seen from this example, in which the data of Table 1 were obtained by testing the solution of uricase in phosphate buffer produced by the aforesaid Enzymatic Ltd. of Cambridge (U.K.) with and without aspartic acid:

TABLE 1

|  | residual activity after 40 minutes at 60° C. |
|---|---|
| Phosphate buffer alone | 22% |
| Phosphate buffer with aspartic acid | 55% |

As stated, the production of hydrogen peroxide during the reaction, catalyzed by uricase, in which uric acid is converted to allantoin, enables it to be combined with a Trinder reaction for colorimetrically measuring the hydrogen peroxide produced, i.e.:

$2H_2O_2$ + chromogens $\xrightarrow{\text{Peroxidase}}$ Quinonimine + $4H_2O$

A Trinder reaction signifies generically a reaction in which evolved hydrogen peroxide is measured colorimetrically using the enzyme peroxidase and particular chromogens. For more complete details of the Trinder reaction reference should be made to U.S. Pat. No. 5,108,733 of Apr. 28, 1992 in the name of the present applicant, which is to be considered as incorporated herein for reference.

Liquid preparations useful for the clinical determination of uric acid containing the enzyme uricase, the Trinder reagent and one of the aforementioned substituted or unsubstituted dicarboxylic acids were tested in this manner.

The tests showed that some of the carboxylic acids useful for stabilizing uricase in solution can negatively influence the functioning of the enzyme peroxidase present in the Trinder reagent, so making the formulation of a reagent involving the use of this latter enzyme to exploit the produced hydrogen peroxide for analytical purposes improbable.

Aspartic acid has proved to be better than the other dicarboxylic acids in performing the double function of significantly stabilizing the enzyme uricase while not interfering with the Trinder reagent.

The following example provides certain interesting experimental data relating to accelerated stability tests for demonstrating the functionality of a ready-to-use single reagent suitable for uric acid determination containing a Trinder reagent and stabilized with aspartic acid.

EXAMPLE 4

The following formulation was used:

| Aspartic acid | 750 mM |
|---|---|
| DPTA (diethylenetriaminepentaacetic acid) | 2.5 mM |
| NaOH | to pH 8.0 |
| TOOS [N-ethyl-N-(2-hydroxy-3-sulphopropyl)-m-toluidine] | 2.4 mM |
| 4-AA (4-aminoantipyrine) | 1.6 mM |
| Sodium azide | 1 g/l |
| Peroxidase | 5000 U/l |
| Uricase | 600 U/l |

For information on the use of DPTA as an inhibitor for the spontaneous coloration of Trinder reagents, reference should be made to the cited U.S. Pat. No. 5,108,733. TOOS and 4-AA represent the chromogens of the Trinder reagent, while sodium azide is an antimicrobic.

Within the pH range of 6.5–10, pH 8 was identified as proximate to the optimum value for both reactions.

Again for this type of liquid composition, a dicarboxylic acid concentration of 500 mM was identified as the value about which the stabilizing activity of the dicarboxylic acid on the enzyme begins to manifest itself.

A dicarboxylic acid concentration of 750 mM was again identified as the value about which the stabilizing activity of the dicarboxylic acid is greatest without any interference occurring with the Trinder reagent contained in the composition. The experiments also showed that the ratio of millimoles/liter of stabilizer to units/liter of enzyme can vary from 1:1 to 1:0.2 without any appreciable change in enzyme stability being noted. The analyses and functionality tests were performed with the Monarch Chemistry Analyzer, manufactured by the present applicant. Non-stabilized lyophilized reagent was used as reference for the uric acid determination.

The instrument test data are as follows:
Temperature: 37° C.
Sample volume: 8 μl Sample diluent: 32 μl
Reagent volume: 50 μl
Reagent diluent: 110 μl
Method: bichromatism (final-initial): 690 nm; 550 nm
Delay: 235 sec
interval: 15 sec
Single point calibration: 6 mg/dl For the linearity, Preciset Biochemia standards of 2, 6, 12 mg/dl of uric acid were used, the 20 mg/dl point being prepared in the laboratory.

The standards were used with reference to the physiological and pathological uric acid concentration range in the serum, i.e. 2–6 mg/dl and >6 mg/dl.

Each value is the median of three repeat tests.

The data obtained are shown in Table 2.

TABLE 2

|  | Ref. | Tzero | Stabilized reagent | | | | |
|---|---|---|---|---|---|---|---|
|  |  |  | 45° | | | 37° | |
|  |  |  | 1 day | 2 days | 3 days | 7 days | 10 days |
| Water | 0 | 0 | 0 | 0 | 0 | 0 | 0 |
| Std 2 | 2.0 | 2.0 | 2.0 | 1.9 | 1.9 | 2.0 | 2.0 |
| Precinorm U | 4.3 | 4.0 | 4.0 | 4.0 | 4.0 | 4.1 | 4.1 |
| Std 6 | 6.1 | 6.2 | 6.2 | 6.1 | 6.1 | 6.1 | 6.2 |
| Precipath U | 11.0 | 10.9 | 10.6 | 10.3 | 10.0 | 10.3 | 10.3 |
| Std 12 | 12.3 | 12.6 | 12.5 | 12.1 | 11.9 | 12.4 | 12.3 |
| Std 20 | 20.5 | 20.4 | 20.2 | 19.3 | 17.8 | 19.7 | 18.9 |
| Absorb. blank reag. | 7 | 7 | 24 | 31 | 31 | 28 | 31 |

Precinorm U and Precipath U are commercially available control sera with uric acid concentrations of 4.2 and 10.3 mg/dl respectively.

From the data of Table 2 there is clear numerical evidence of the stabilizing effect of aspartic acid on the activity of a liquid composition containing a Trinder reagent.

From the last item in the table relative to the absorbance measured on the liquid composition as such, a further significant effect of aspartic acid on this type of uricase liquid composition emerges, i.e., that the addition of the stabilizer also acts in the sense of inhibiting spontaneous coloration of the reagent. The experiments also showed identical stabilizing capacity for both stereoisomers of aspartic acid.

Finally, the experiments show that the 450 and 600 nm spectra curves for the reference reagent, with and without aspartic acid as stabilizer, after reacting the reagent with uric acid, are practically identical. This practical identity between the two curves indicates that the presence of the stabilizer does not interfere in any way with the progress of the two aforesaid reactions.

We claim:

1. A method for stabilizing a liquid preparation of the enzyme uricase, comprising introducing into the preparation a dicarboxylic acid containing about 2 to 5 carbon atoms, to produce a concentration of said dicarboxylic acid which exceeds 500 mM.

2. The method of claim 1, wherein the dicarboxylic acid contains 4 or 5 carbon atoms.

3. The method of claim 1, wherein the amount of uricase in said preparation is between about 0.2 and 3.0 U per 1 mM of the dicarboxylic acid.

4. The method of claim 1, wherein the dicarboxylic acid concentration is about 750 mM/l.

5. The method of claim 2, wherein the dicarboxylic acid is aspartic acid.

6. The method of claim 2, wherein the liquid preparation further comprises a Trinder reagent suitable for the colorimetric determination of hydrogen peroxide produced during the course of a reaction catalyzed by the uricase.

7. The method of claim 6, wherein the dicarboxylic acid is aspartic acid.

8. The method of claim 7, wherein the pH of the liquid preparation is within the range of about 6.5–10.0.

9. The method of claim 7, wherein the amount of uricase is between about 0.2 and 1.0 U per 1.0 mM of the dicarboxylic acid.

10. The method of claim 7, wherein the aspartic acid concentration is about 750 mM/l.

11. A stabilized liquid preparation of the enzyme uricase, comprising uricase and a dicarboxylic acid containing about 2 to 5 carbon atoms;
   wherein the dicarboxylic acid concentration exceeds 500 mM.

12. The stabilized liquid preparation of claim 11, wherein the dicarboxylic acid contains 4 or 5 carbon atoms.

13. The stabilized liquid preparation of claim 11, wherein the amount of uricase in the preparation is between about 0.2 and 3.0 U per 1.0 mM of the dicarboxylic acid.

14. The stabilized liquid preparation of claim 12, wherein the dicarboxylic acid concentration is about 750 mM/l.

15. The stabilized liquid preparation of claim 12, wherein the dicarboxylic acid is aspartic acid.

16. The stabilized liquid preparation of claim 12, further comprising a Trinder reagent suitable for the colorimetric determination of hydrogen peroxide produced during the course of a reaction catalyzed by the uricase.

17. The stabilized liquid preparation of claim 16, wherein the dicarboxylic acid is aspartic acid.

18. The stabilized liquid preparation of claim 17, wherein the pH of the liquid preparation is within the range of about 6.5–10.0.

19. The stabilized liquid preparation of claim 17, wherein the amount of uricase in the preparation is between about 0.2 and 1.0 U per 1.0 mM of the dicarboxylic acid.

20. The stabilized liquid preparation of claim 17, wherein the aspartic acid concentration is about 750 mM/l.

* * * * *